United States Patent
Bigalke

(10) Patent No.: US 7,272,981 B2
(45) Date of Patent: Sep. 25, 2007

(54) ASEPTIC FLUID SAMPLER AND METHOD

(76) Inventor: Darrell Lee Bigalke, 11395 Irish Ave. North, Stillwater, MN (US) 55082

( * ) Notice: Subject to any disclaimer, the term of this patent is extended or adjusted under 35 U.S.C. 154(b) by 0 days.

(21) Appl. No.: 11/605,704

(22) Filed: Nov. 29, 2006

(65) Prior Publication Data

US 2007/0089541 A1    Apr. 26, 2007

Related U.S. Application Data

(60) Division of application No. 11/156,671, filed on Jun. 20, 2005, which is a division of application No. 10/875,842, filed on Jun. 24, 2004, which is a continuation-in-part of application No. 10/022,294, filed on Dec. 14, 2001, now Pat. No. 6,845,676.

(51) Int. Cl.
 *G01N 1/10* (2006.01)
(52) U.S. Cl. .................................. 73/863.85
(58) Field of Classification Search . 73/863.85–863.86
 See application file for complete search history.

(56) References Cited

U.S. PATENT DOCUMENTS

| | | | |
|---|---|---|---|
| 3,534,613 A | 2/1969 | Travor et al. | 73/863.85 |
| 3,776,042 A | 12/1973 | Werra et al. | 73/863.85 |
| 3,779,082 A | 12/1973 | Galloway | 73/863.85 |
| 4,785,676 A | 11/1988 | DeOca et al. | 73/863.85 |
| 4,941,517 A | 7/1990 | Galloway | 73/863.85 X |
| 5,049,492 A | 9/1991 | Sauer et al. | 73/863.85 X |
| 5,086,813 A | 2/1992 | Galloway | 73/863.85 X |
| 5,119,473 A | 6/1992 | Ikenoue | 358/1.16 |
| 5,133,938 A | 7/1992 | Glanville et al. | 73/863.85 X |
| 5,269,350 A | 12/1993 | Galloway | 141/11 |
| 5,296,197 A | 3/1994 | Newberg et al. | 73/863.85 X |
| 5,474,546 A | 12/1995 | Ambrisco et al. | 604/411 |
| 5,604,320 A | 2/1997 | Boyd | 73/863.86 |
| 5,673,737 A | 10/1997 | Behnke et al. | 73/863.86 X |
| 5,743,209 A | 4/1998 | Bazin et al. | 119/14.08 |
| 5,803,078 A | 9/1998 | Brauner | 128/207.14 |
| 5,823,134 A | 10/1998 | van den Berg | 119/14.02 |
| 5,823,222 A | 10/1998 | Minshull et al. | 73/863.86 X |

(Continued)

FOREIGN PATENT DOCUMENTS

WO    WO96/03859    2/1996

(Continued)

OTHER PUBLICATIONS

"Keofitt World Leaders in Sterile Sampling", 4 pages by Dec. 2001.

(Continued)

*Primary Examiner*—Thomas P. Noland
(74) *Attorney, Agent, or Firm*—Merchant & Gould P.C.

(57) ABSTRACT

An aseptic sampling arrangement that provides selective access to an interior of a fluid enclosure. The sampling arrangement includes a septum cartridge and a securing element for use with the fluid enclosure. A locking arrangement is provided to allow selective access to the septum cartridge and the securing element. The locking arrangement includes a base, a cover, and a locking device that secures the cover in relation to the base.

24 Claims, 7 Drawing Sheets

U.S. PATENT DOCUMENTS

| | | | |
|---|---|---|---|
| 6,032,543 A | 3/2000 | Arthun et al. | 73/863.84 |
| H1960 H | 6/2001 | Conrad et al. | 73/864.82 |
| 6,287,289 B1 | 9/2001 | Niedospial, Jr. | 604/408 |
| 6,511,688 B2 | 1/2003 | Edwards et al. | 426/130 |
| 6,521,451 B2 | 2/2003 | Potter | 435/383 |
| 6,622,882 B2 | 9/2003 | Smith | 250/259.1 |
| 6,845,676 B2 | 1/2005 | Bigalke | 73/863.85 |
| 7,044,010 B2 | 5/2006 | Bigalke | 73/863.85 X |
| 7,082,848 B2 | 8/2006 | Fjerdingstad | 73/863.85 |
| 7,155,989 B1 * | 1/2007 | Gerold et al. | 73/863.85 |
| 2002/0033057 A1 | 3/2002 | Egas et al. | 73/863.86 |
| 2003/0101830 A1 | 6/2003 | Wickland et al. | 73/863.85 |
| 2004/0210162 A1 | 10/2004 | Wyatt et al. | 600/573 |
| 2004/0228953 A1 | 11/2004 | Bigalke | 426/231 |
| 2005/0066750 A1 | 3/2005 | Bigalke | 73/863.85 |
| 2005/0260695 A1 | 11/2005 | Fleming et al. | 435/7.93 |

FOREIGN PATENT DOCUMENTS

WO     WO 00/33901     6/2000

OTHER PUBLICATIONS

Liquid Sampling Systems, Inc., Cedar Rapids, IA, "The Pro-Rata™ Line Sampler, The future of dairy sampling-today", 4 pages, by Dec. 2001.

Tate, J.L., "The Art of Managing Contamination", *Pharmaceutical Processing*, 4 pages (Jan. 2000).

Jones, G.M. et al, Testing Bulk Tank Milk Samples, Virginia Cooperative Extension, available at http://www.ext.vt.duc/pubs/dairy/404-405/404-405.html. posted Mar. 1999, pp. 1-8.

\* cited by examiner

ASEPTIC FLUID SAMPLER AND METHOD

CROSS-REFERENCE TO RELATED APPLICATIONS

This application is a divisional of application Ser. No. 11/156,671, filed Jun. 20, 2005; which is a divisional of application Ser. No. 10/875,842, filed Jun. 24, 2004; which is a continuation-in-part of application Ser. No. 10/022,294, filed Dec. 14, 2001, now U.S. Pat. No. 6,845,676; which applications are incorporated herein by reference.

FIELD OF THE INVENTION

This disclosure concerns a sampling arrangement. More specifically, this disclosure describes the assembly and method of use of a sampling arrangement for aseptic, continuous sampling of a fluid material.

BACKGROUND OF THE INVENTION

There are numerous applications wherein it is desirable to obtain discrete or continuous samples from fluid transportation systems or fluid processing enclosures. Enclosures and fluid transportation systems, as used herein, refer to any closed containment structure without respect to its size. Thus it includes such small enclosures such as cans that may be used in shipping starter bacteria from a culture lab. On the other end of the spectrum, it includes large tanks and associated pipelines, which may have capacities of several thousand gallons, such as are used in the dairy processing industry.

Efficient and effective techniques and apparatus for obtaining aseptic samples from such systems and enclosures, are particularly desirable. Examples of industries that require such aseptic sampling include, but are not limited to, the pharmaceutical, bioengineering/biotechnology, brewing/distilling, food processing and dairy processing industries. Applications for such samplings range broadly from process monitoring to laboratory and research applications. For example, sampling is commonly used on dairy farms for herd management or in regulated manufacturing facilities. The sampling is used to detect and control microbial contamination, spoilage microorganisms, food-borne illness, and environmental mastitis both within systems being sampled and externally of such systems. While preferred embodiments of this invention will be described with respect to its sampling use and application in the dairy industry, it will be understood that the invention is not to be construed as limited to use in that industry or to the application described, or to any limitations associated with the specifics of the components or methods disclosed with respect to such preferred embodiments.

Various methods and devices have been employed to perform sampling tasks. Typical sampling techniques commonly involve discrete or isolated sampling from a laminar portion of a fluid transport line. Typical such sampling systems and techniques that have been used in the dairy processing industry are described in U.S. Pat. Nos. 4,941,517; 5,086,813; and 5,269,350. To the extent that such patents may be used to assist the reader in understanding principles and examples of sampling apparatus and methods, they are herein incorporated by reference.

While the apparatus and techniques described in these patents are particularly applicable to systems designed to accommodate them, there also exists a need to perform sampling in existing enclosures and fluid transportation systems that have not been designed for sampling functions. Such systems typically require redesign or retrofitting to accommodate sampling functions. Such retrofitting can be expensive and/or difficult to achieve, can require significant system downtime in implementation of the sampling function and/or replacement of parts to maintain the system, or can lead to system degradation or contamination of the system being sampled. For example, one known method of discrete sampling of fluid involves inserting a needle through a sealing gasket located between connecting ends of pipelines of the fluid transportation system. Problems arises from this method as this method is not aseptic because the gasket becomes so perforated after repeated sampling that the gasket may lose its sealing integrity or introduce contaminants into the system through the perforations. This method requires that the gasket be replaced, which can become expensive both in labor costs and shut down costs.

There are many applications wherein it is desirable to obtain a continuous sample from fluid transportation systems or fluid processing enclosures. The discrete sampling methods typically extract a discrete sample size limited to the volume of a hypodermic needle and syringe. Typically the needle is inserted, fluid is drawn, and the needle is removed. It would be beneficial in some applications to have a system that could draw a continuous, controlled and constant sample volume over an extended period of time. A sampling device that facilitates this feature would also need to accommodate larger volume samples and a means to cool the sample during longer sampling time periods. While continuous sampling techniques have been tried, they have generally not been particularly effective, efficient or reliable in maintaining the aseptic condition of the system during the sampling interval.

Known discrete sampling techniques have not proven to be readily adaptable to continuous sampling techniques. For example, if the sample is taken from a region of laminar fluid flow, the sampling needle can create a venturi effect in the fluid flow being sampled, which can cause reverse flow siphoning from the collected sample and back into the sampled fluid. If such suction effect is disrupted by providing the sampling system with an air gap, the aseptic nature of the sampling system is compromised.

Improvement in methods and devices for sampling is needed, generally to better accommodate: ease of repeated continuous sampling of large volumes; structural integrity of fluid transport equipment; management of contamination; and convenience of continuous and controlled volume sampling. The present invention addresses these and other needs for continuous sampling of fluid transportation systems or fluid processing enclosures.

SUMMARY OF THE INVENTION

One aspect of the present disclosure relates to a method of monitoring quality of a fluid product. The method includes providing an aseptic sampling arrangement including a septum and a collection bag. A sample of the fluid product is obtained by aseptically collecting the fluid product in the collection bag. The collection bag is incubated for a period of time. The method also includes monitoring the level of contamination within the sample of fluid product during the period of time.

Another aspect of the present disclosure relates to a sampling arrangement for use with a fluid enclosure. The sampling arrangement includes a septum configured for receipt within an aperture of the fluid enclosure. The septum is constructed for penetration of a needle therethrough to provide fluid communication between an internal volume of the fluid enclosure and a collection bag. The sampling arrangement also includes a locking arrangement configured to provide selective access to the septum.

Yet another aspect of the present disclosure relates to a sampling arrangement having a septum, a securing element, and a locking arrangement. The septum is configured for receipt within an aperture of a fluid enclosure. The securing element configured to secure the septum within the aperture of the fluid enclosure. The locking arrangement includes a base, a cover, and a locking device, and is configured to provide selective access to the septum and the securing element.

Still another aspect of the present disclosure relates to a fluid system including a fluid enclosure, an aseptic sampling arrangement, and a locking arrangement. The aseptic sampling arrangement has a septum and a securing element, the septum being secured within an aperture of the fluid enclosure by the securing element. The locking arrangement provides selective access to the sampling arrangement.

And another aspect of the present disclosure relates to a method of providing access to a fluid enclosure. The method includes positioning a septum of an aseptic sampling arrangement within an aperture of the fluid enclosure and securing the septum within the aperture of the fluid enclosure with a securing element. The method further includes enclosing the septum and the securing element within a locking arrangement to prevent unwanted access to the septum and the securing element and locking the locking arrangement to permit only selective access to the septum and the securing element.

A variety of examples of desirable product features or methods are set forth in part in the description that follows, and in part will be apparent from the description, or may be learned by practicing various aspects of the disclosure. The aspects of the disclosure may relate to individual features as well as combinations of features. It is to be understood that both the foregoing general description and the following detailed description are explanatory only, and are not restrictive of the claimed invention.

BRIEF DESCRIPTION OF THE DRAWINGS

Referring to the drawings wherein like numerals represent like parts throughout the several views.

DETAILED DESCRIPTION

Figure 1:
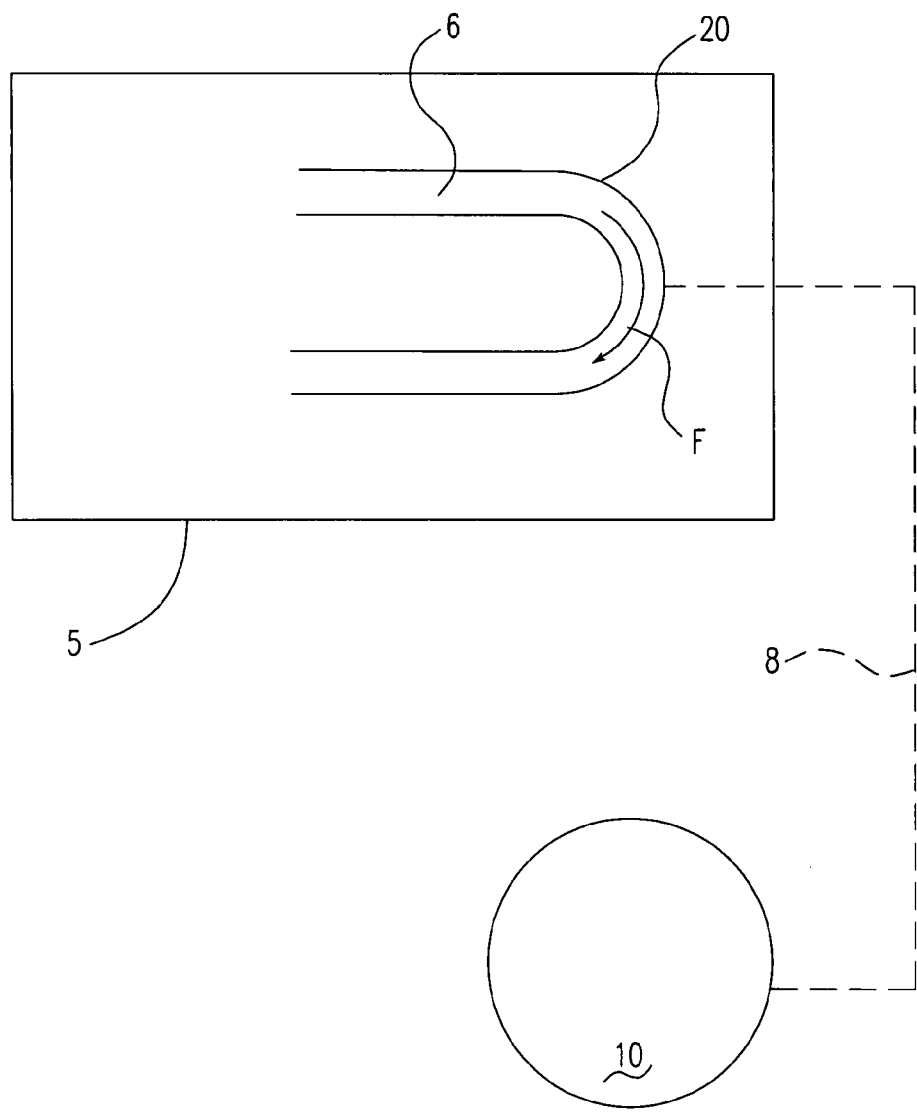
FIG. 1 is a schematic illustration of a system incorporating a continuous sampling arrangement in accordance with the principles disclosed.

This invention provides an apparatus and method for the continuous aseptic sampling of fluid material from a fluid transportation system or fluid processing enclosure 5, schematically illustrated in FIG. 1. A fluid material 6 to be sampled is illustrated as flowing through a fluid line 20 by the fluid flow arrow designation "F". A preferred sampling arrangement of the present invention is schematically illustrated at 10 and is depicted as operatively connected, by the dashed line 8, to sample the fluid material 6 (as hereinafter described in more detail).

The principles described herein for the sampling arrangement 10 can be used in various industries and in various applications where aseptic sampling of material is desired. Aseptic sampling involves transferring fluids to or from process systems that are sensitive to contamination from the outside environment. For example, the pharmaceutical, bioengineering/biotechnology, brewing/distilling, food processing and dairy processing industries are in need of aseptic sampling technology. Such sampling technology can be applied broadly, the applications ranging from process monitoring to laboratory and research applications. For example, the fluid processing enclosure or fluid transportation system 5 illustrated in FIG. 1 may comprise a dairy processing system used in the dairy industry. An example of one type of fluid processing enclosure or fluid transportation system 5 that has been used in the dairy processing industry is described in U.S. Pat. No. 5,269,350 and herein incorporated by reference. In such a system, the fluid material 6 therein may include raw milk or a processed milk product. The sampling arrangement 10 may be incorporated or retrofitted to the fluid transportation system 5 to provide continuous aseptic sampling for detecting microbial contamination or monitoring mastitis, coliform, food-borne illness bacteria, or spoilage bacteria in a dairy herd, for example.

While preferred embodiments of this invention will be described with respect to its sampling use and application in the dairy industry, it will be understood that the invention is not to be construed as limited to use in that industry or to the particular application described.

The Structural Components, Generally.

Figure 2:
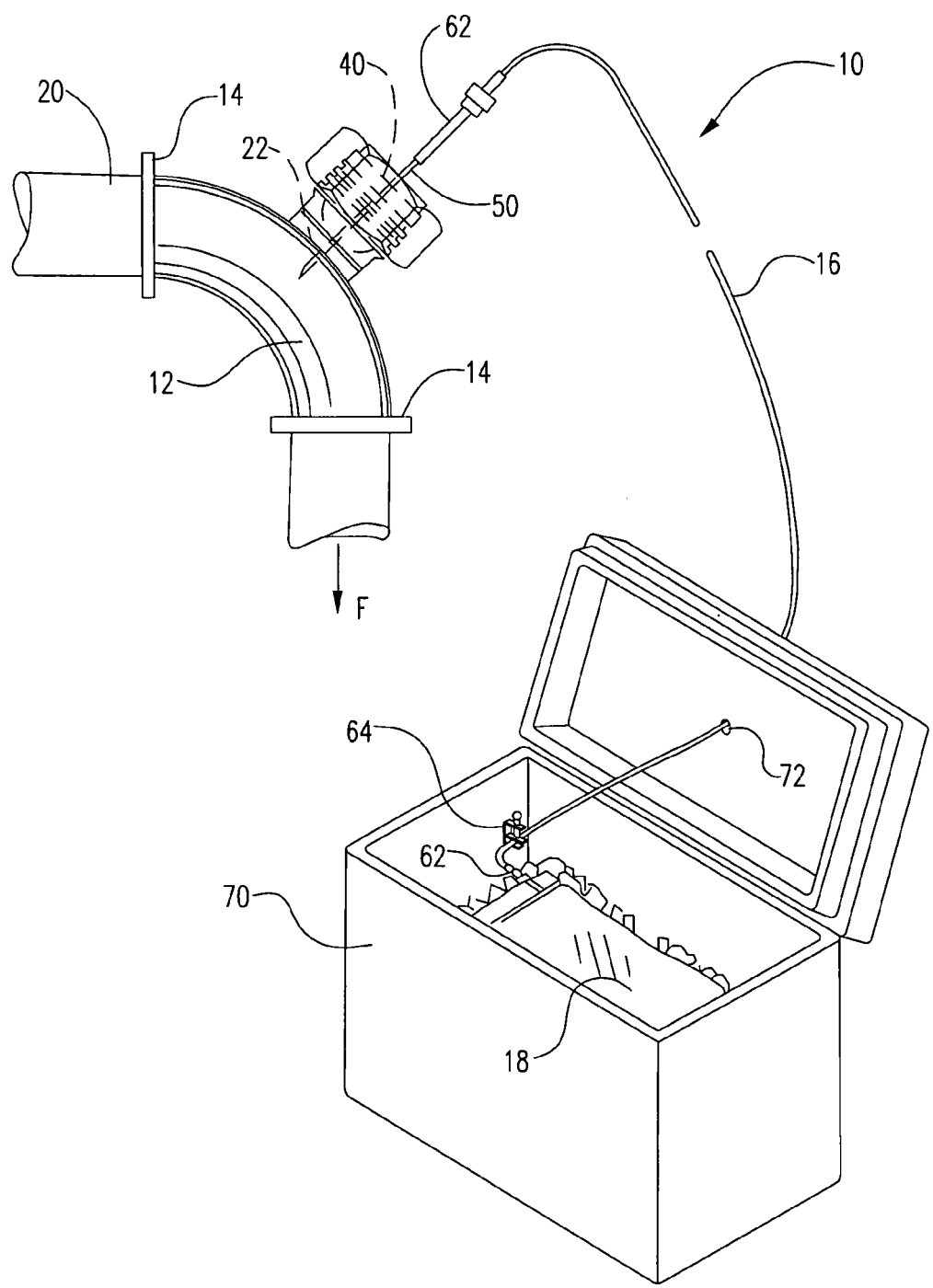
FIG. 2 is a detailed schematic illustration of one embodiment of the continuous sampling arrangement in accordance with the principles disclosed.

Referring to FIG. 2, the preferred sampling arrangement 10 depicted includes: an elbow 12 having flanges 14 and a port 22; a least one septum or septum cartridge 40 (shown in phantom); a connecting conduit 16; and a collection container 18. In general, the sampling arrangement 10 comprises an arrangement that provides for a continuous draw of fluid from a flow F within a fluid line 20, and deposits the fluid sample in the collection container 18 to provide the user with an accumulated process sample. It is to be understood that the fluid line 20 may comprise a variety of fluid transportation systems or fluid containment enclosures, and is not limited to pipe constructions. The collection container 18 may include a pouch, bag, reservoir, or other closed container of a typical construction and size, such as those used in the medical industry. In the illustrated embodiment, a medical type bag comprising a 2-liter collection pouch or bag is used. A variety of sizes and constructions of containers is contemplated.

As illustrated, the pipe segment or elbow 12 of the sampling arrangement 10 is in direct fluid communication with the fluid line 20 of the fluid transportation system. In accordance with the principles of the present invention, it is desirable to perform sampling from an area or region of non-laminar flow within the line 20. The elbow 12 provides a turbulent or non-laminar flow region within its interior flow cavity by its non-linear configuration. It is to be understood that there are other means of creating a non-laminar flow region within the fluid flow line, such as having a protrusion or device extending into the flowing fluid within a substantially straight portion of the fluid line. Therein fluid turbulence or non-laminar flow is formed downstream of the extending device or protrusion. Creation of a non-laminar sampling region eliminates the problem of reversed fluid flow from the sample to the main fluid line, which commonly occurs in devices and methods of the prior art.

Figure 3:
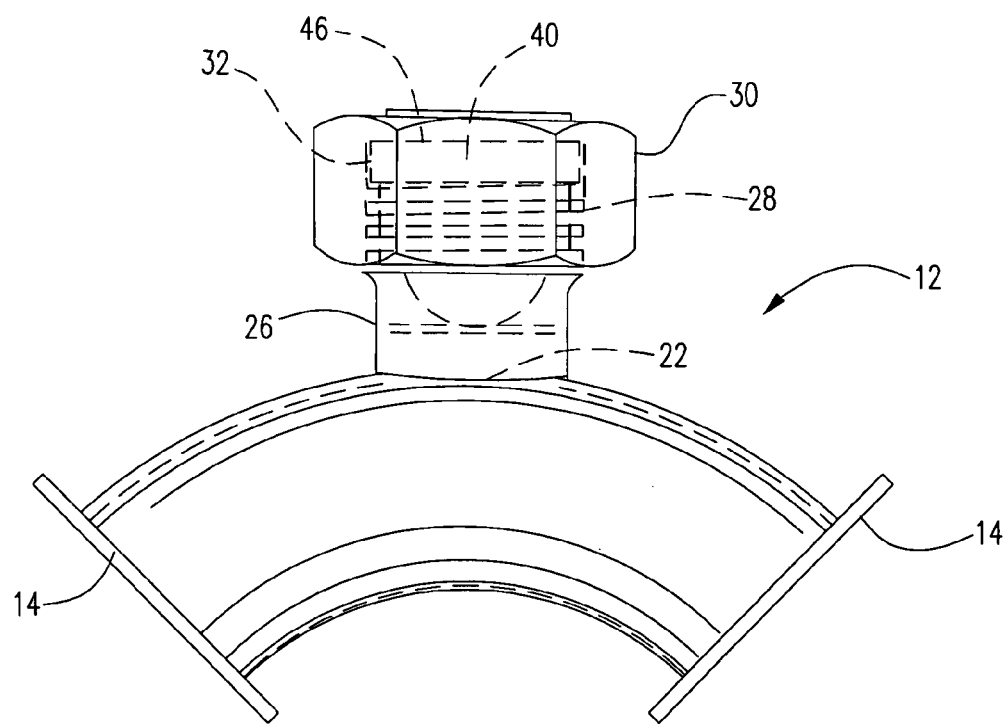
FIG. 3 is a side view of a pipe elbow depicted in the sampling arrangement of FIG. 2.
Figure 4:
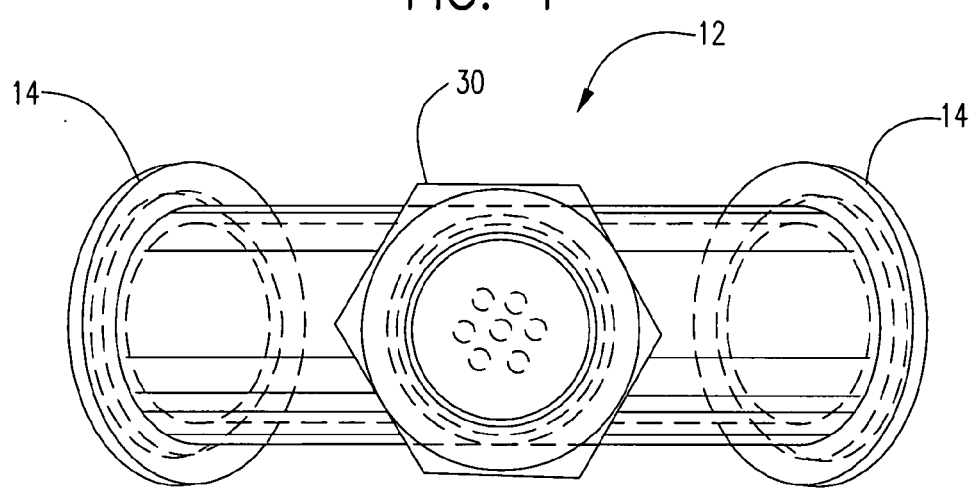
FIG. 4 is a top view of the pipe elbow depicted in FIG. 3.

Referring now to FIGS. 3 and 4, the connection flanges 14 of the elbow 12 extend circumferentially at each end of the elbow 12. The flanges 14 may include grooves (shown in phantom) sized to receive sealing gaskets (not shown) to seal the connections between pipe segments when installed in common fluid transportation line systems. In accord with the principles of the present invention, the sampling arrangement is generally adapted to be retrofitted within existing fluid lines of various fluid flow systems 5 (FIG. 1). Certainly the sampling arrangement 10 can be incorporated as original equipment into new installations of fluid transportation lines as well. Other means of connection or retrofit adaptation, including welding, are contemplated as a means of installation. The sampling arrangement is generally designed with standard plumbing components to facilitate retrofit modifications. It is to be understood that non-standard elements, such as non-standard pipe diameter, fittings, or material, are within the scope of the principles disclosed.

Preferably the elbow 12 is made of industry standard stainless steel, such as 304 or 316L stainless steel. Other materials applicable for use in the industry into which the sampling arrangement is implemented are contemplated. The elbow depicted in FIG. 3 incorporates a standard 90-degree elbow. The angular configuration of the elbow will typically be a standard dimension within the range of 35 degrees to 180 degrees, typically 90 degrees. The preferred diameter of the elbow pipe is at least 1 inch, typically from about 1.5 to 3.5 inches in diameter.

The elbow 12 according to the present invention includes at least one aperture or port 22. The elbow 12 may be located in any configuration in the fluid transportation system where the port 22 is operably in fluid communication with the fluid material 6 within the system. Thus, the interior angle of the elbow 12 may be oriented, for example, upward, downward or sideways in a fluid line arrangement. It is also contemplated that to ensure that the port is operably in fluid communication with the fluid material 6, the port 22 may be configured in alternative locations on the elbow 12. In the illustrated embodiment, the port 22 is located on the outer radius of the elbow 12. Alternative embodiments may include, for example, an elbow having a port located on the interior radius of the elbow. Preferably, the port 22 is disposed at or within a non-laminar flow region of the elbow 12.

As depicted in FIG. 3, the port 22 may include a transversely extending pipe portion or conduit 26. The conduit 26 is sized to receive a septum cartridge 40. The conduit 26 may include an externally threaded region 28 for purposes of securing the septum cartridge 40. In one embodiment, the thread comprises a standard 1.5"-8 ACME thread corresponding to a mating internally threaded nut 30. The threaded nut 30 may include an internal annular shoulder 32 (shown in phantom). The annular shoulder 32 acts as a bearing surface that engages a first surface 46 of the septum cartridge 40 (shown also in FIG. 7) to secure the septum cartridge in sealing manner when assembled within the port 22. Other types of fasteners commonly used as securing or retaining means within this context are contemplated and may include, for example, a hex nut, a knurled lock nut, or a keyed nut.

Figure 5:
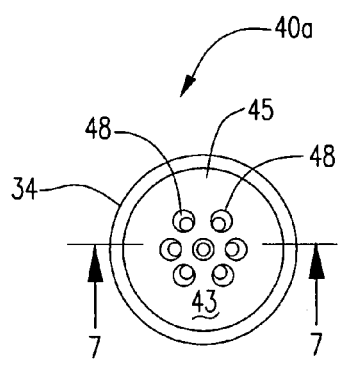
FIG. 5 is a top view of one embodiment of a septum used in the sampling arrangement of FIG. 2.
Figure 6:
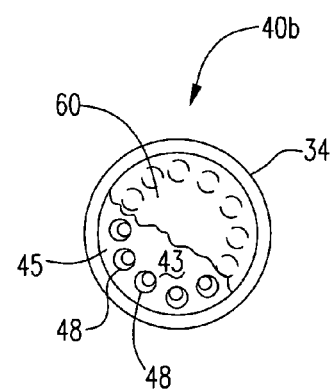
FIG. 6 is a top fractional view of another embodiment of a septum used in the sampling arrangement of FIG. 2.
Figure 7:
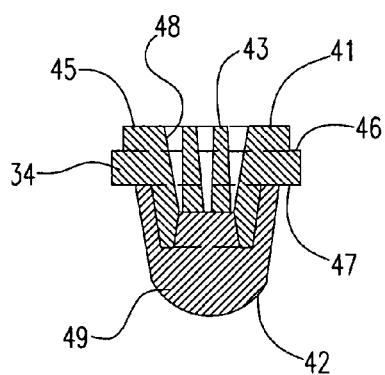
FIG. 7 is a cross sectional view of the septum shown in FIG. 5, taken generally along line 7-7 of FIG. 5.

Referring generally to FIG. 2, the septum cartridge 40 is in fluid communication with the interior cavity of the fluid line 20 by means of the aperture or port 22 in the elbow 12. As shown in FIGS. 5-7, the septum cartridge 40 generally comprises a cap 45, a central core member or boot 49, and a plurality of guide holes 48 formed through the cap. For purposes of clarifying features, the septum cartridge 40 can be considered to have a top 41 and a bottom 42.

The cross-section of the boot 49 is seen to increase progressively from the bottom 42 toward the top 41 of the septum cartridge 40. The boot 49 is sized such that when the boot is placed within the port 22 of the elbow there is compressive contact between the interior surfaces defining the port 22 and the boot 49. The boot thereby functions as a sealing member. The boot 49 illustrated is generally conical, but could adopt a variety of shapes as will be obvious from the following discussion of the functioning of the septum cartridge in combination with other components of the invention.

The boot 49 may be made of material that is generally considered to be of a rubber compound. While compounding of an acceptable rubber composition is believed to be within the skill of the rubber molding art, it is found that rubber compounds based on ethylene propylene diene monomer terpolymer (EPDM) are particularly advantageous, having suitable sealing characteristics. EPDM is a known elastomer, and recognized by those skilled in the polymer arts. Other elastomers are contemplated, such as those derived from, or modified with, butene isoprene, ethylene, and the like. In an alternative embodiment, the boot may comprise a silicone compound. Silicone also provides suitable sealing characteristics. Materials such as Viton or other FDA approved elastomers are also contemplated for use in manufacture of the boot.

Preferably, the cap 45 includes an annular radially extending portion 34 defining the first upwardly oriented surface 46 and an opposing second lower surface 47. The outer diameter of the annular portion 34 is preferably only slightly less than the inner diameter of the internal shoulder 32 on the threaded nut 30 for purposes of engaging and retaining the septum cartridge 40 within the port 22 of the elbow in the sampling arrangement 10.

The cap 45 is made of a material that is normally not penetrable by conventional hypodermic needles. A typical material for fabrication of the cap may include one of the engineering plastics, such as nylon, polypropylene, or high-density polyethylene. The penetrability of the septum cartridge 40 is thus provided by one or more of the integrally formed guide holes 48, which begin from a top surface 43 of the cap 45 and extend downwardly through the cap 45.

The guide holes 48 are integral with the cap 45 and located to correspond to the boot 49. The guide holes 48 extend downwardly through the cap structure 45 and are oriented and positioned so that a sampling needle 50 (shown in FIG. 8) may pass through the guide hole 48 and into the boot 49. The guide holes 48 are generally sized to be only slightly larger than the needle, such that the needle slidably fits snugly within the guide hole, preferably without substantial friction, but with a close enough fit to ensure that the guide hole provides direction to the needle as it is inserted through the boot. In one embodiment (FIG. 5), the septum cartridge 40a includes seven guide holes. In another embodiment (FIG. 6), the septum cartridge 40b includes twelve guide holes. Typically the septum cartridge includes at least one guide hole, generally 1 to 15 guide holes.

A cover film 60 covers the top surface 43 of the cap 45, including the guide holes 48 formed in the top surface 43 of the cap 45. The cover film 60 easily identifies used holes to reduce the risk of contamination from reinserting a needle into a previously used guide hole. The cover film 60 may be made from any readily pierceable film material. A typical film material is a vinyl tape having an adhesive coating to securely attach the cover film 60 to the top surface of the cap 45.

Figure 8:
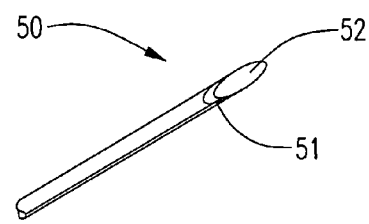
FIG. 8 is a fragmentary perspective view of a needle depicted in the sampling arrangement of FIG. 2.

Referring to FIGS. 2 and 8, the penetrating body or needle 50 is in fluid communication with the connecting conduit 16, and the connecting conduit 16 is in fluid communication with the collection container 18. In the preferred embodiment, the needle comprises a beveled end 51 having an aperture 52 that defines a hollow portion running longitudinally through the needle 50. It is to be understood that other penetrating bodies, such as lumens, hollow members, or inserting devices may be used in accordance with the principles disclosed.

In use, the needle 50 penetrates the cover 60, passes through a selected guide hole 48, and penetrates through the boot 49. As the needle penetrates the boot, the needle displaces the elastomeric/rubber material of the boot which forms a fluid impenetrable seal about the needle. The beveled end 51 of the needle 50 progresses through the boot 49 and emerges from the boot at the bottom 42 of the septum cartridge 40. The needle therein enters into the flow of fluid F.

The needle 50 is sized and adapted for use with the septum cartridge 40. Typically the needle comprises a 12 gauge to 22 gauge needle, preferably a 16 gauge needle. The needle generally has a length of from about 1.0 inches to 4.5 inches. Preferably the needle is at least 1.5 inches in length if the port 22 is bottom placement oriented and at least 2.0 inches if the port 22 is top placement oriented. What is meant by top and bottom placement oriented is how the sampling port is oriented with respect to ground. Thus, if the elbow is top placement oriented, a longer needle 50 is needed to ensure the needle aperture 52 is submerged within the fluid material when operatively inserted through the septum 40.

Still referring to FIG. 2, the connecting conduit 16 also includes sealing ends 62 at locations where the fluid flow transitions from the needle 50 to the connecting conduit 16 and from the connecting conduit 16 to the collection container 18. A typical, usable connecting conduit is the type used by the medical industry in fluid administration sets. Conduit in accordance with the principles disclosed includes, for example, tubing, flexible piping or flexible lumen constructions that provide closed, aseptic fluid communication between ends.

Preferably the connecting conduit 16 is of sufficient length to reach from the elbow 12 to an area where the collection container 18 is placed. The length may thus vary and typically falls within the range of 5 inches to 65 inches, and preferably is about 38 inches in length. In one embodiment, the connecting conduit comprises a 0.121 inch inside diameter and a 0.166 outside diameter. It is to be understood that typical fluid administration sets having a needle, connecting conduit, and a collection pouch are contemplated for use in this sampling arrangement.

In use, the needle 50 is inserted through the septum 40 into a non-laminar fluid flow region of the elbow 12. Sampling at a non-laminar fluid flow region addresses the problem of reversed fluid flow often created by a venturi effect of prior sampling systems. The venturi effect is created where the velocity of the laminar fluid flow flowing past an orifice or tube opening (such as in a needle) causes a corresponding decrease in fluid pressure, which creates a siphoning or suction. Thus, instead of drawing sampled fluid from the fluid line into a collection container, sampled fluid is actually drawn from the collection container back into the fluid line. The sampling arrangement 10 of the present invention reduces or eliminates this problem.

Some Selected Alternate Embodiments

Figure 9:
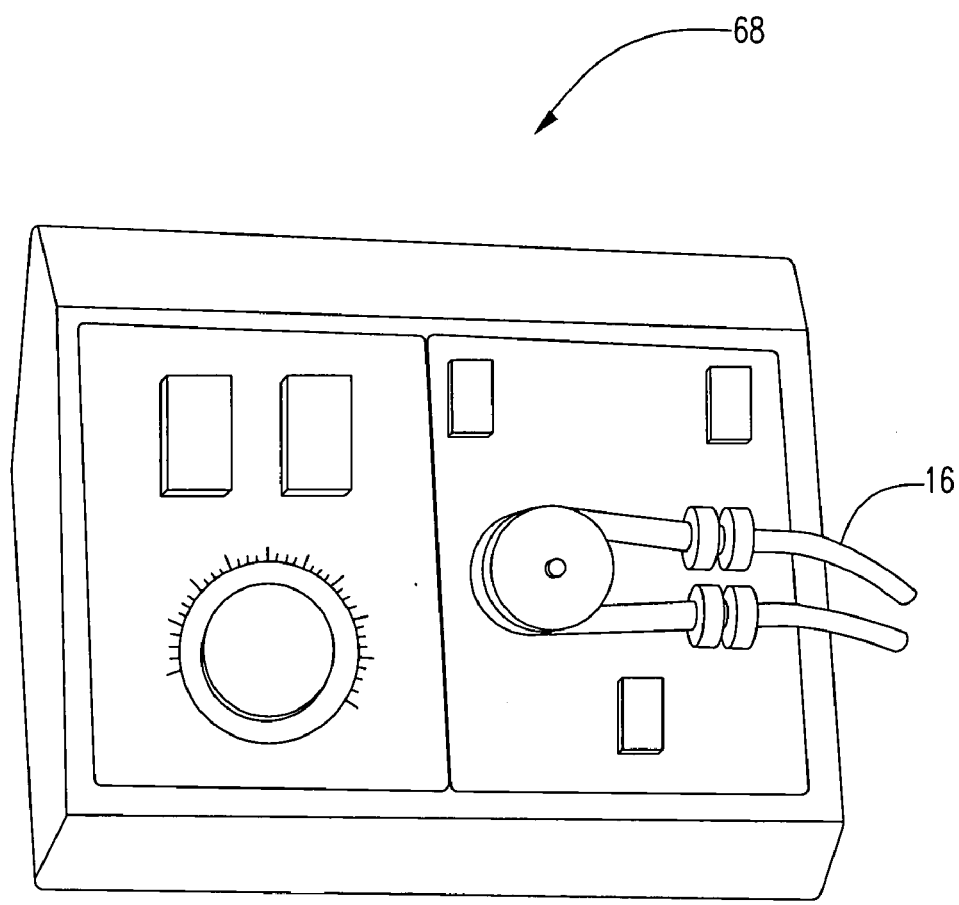
FIG. 9 is an illustration of one embodiment of a regulating device that can be used in the sampling arrangement of the present invention.

Alternative embodiments incorporating the principles of the present invention will be apparent from the description below and in the context of the illustrations in FIGS. 2 and 9.

In one alternative embodiment, the sampling arrangement 10 includes a flow restricting device. The flow restricting device may comprise a clamp 64 as shown in FIG. 2. The clamp 64 compressively engages the outer surface of the connecting conduit 16 and is adjustable such that flow through the tube may be restricted to a desired flow rate. Thereby, the continuous sampling rate may be increased or decreased during sampling as needed.

Another embodiment of the sampling arrangement includes an alternative means of regulating flow. FIG. 9 depicts a fragmented portion of a sampling arrangement including a metering or peristaltic pump 68. The peristaltic pump 68 cooperatively engages connecting conduit 16 and is adjusted as is known in the art to provide a desired regulated flow rate.

The clamp 64 and the peristaltic pump 68 are products of common manufacture. The clamp may comprise any clamping device suitable to provide restriction in the connecting conduit 16. The peristaltic pump may comprise, for example, a variable flow pump having a medium flow rate of 4.0 to 85.0 milliliters per minute. Specifically, a Medium Flow variable flow pump, Model Number 54856-075, manufactured by MASTERFLEX is one variable flow pump that may be used.

Yet another embodiment of the present invention provides for cooling of the extracted sample held by the collection container. If it is desirable to keep the extracted sample cool during collection, the collection container 18 may be placed in an insulated cooler 70 surrounded by ice or cold packs as shown in FIG. 1, for example. Common coolers can be modified to include a hole 72 in the top or lid through which the connecting conduit 16 can be routed.

FIGS. 10-13 illustrates still another embodiment of the present invention including a tamper-resistant locking arrangement 80. As previously described, the disclosed sampling arrangement 10 is coupled to the fluid processing enclosure or fluid handling/transport system 5. In this particular application, the fluid transport system 5 includes, for example, a tank 82. The tank may be any type of fluid-containing tank, such as the fluid processing enclosures 5 previously described, storage tanks, and even over-the-road transportation tanks, such as a tanker truck, for example. The locking arrangement 80 is useful in any application where product tampering or product removal may be of concern. The locking arrangement 80 is also useful in locations or processing areas that are less frequently monitored.

Figure 13:
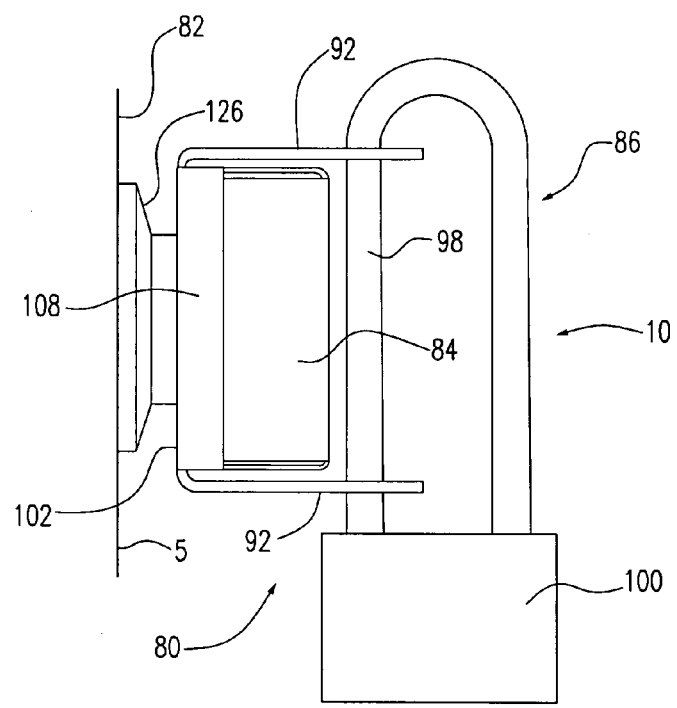
FIG. 13 is a first side view of the locking arrangement of FIG. 10, shown with a locking device.

As shown in FIGS. 10-13, the locking arrangement 80 generally includes a base 102, a cover 84 and a locking device 86 (FIG. 13). The locking arrangement 80 is configured to enclose the threaded nut 30 and septum cartridge 40 (FIGS. 5-7) of the sampling arrangement 10 to prevent unwanted access to the internal volume of the tank 82.

Figure 11:
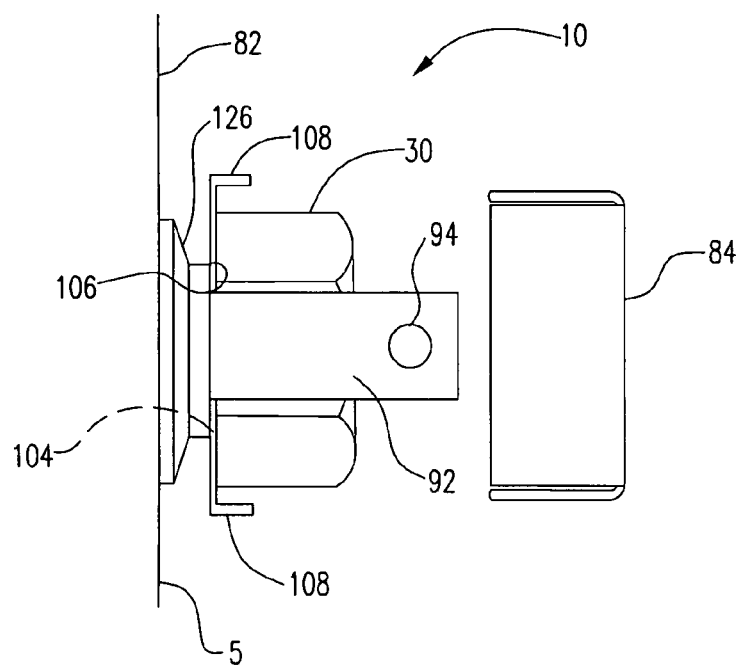
FIG. 11 is a second, partially exploded, side view of the locking arrangement of FIG. 10.
Figure 12:
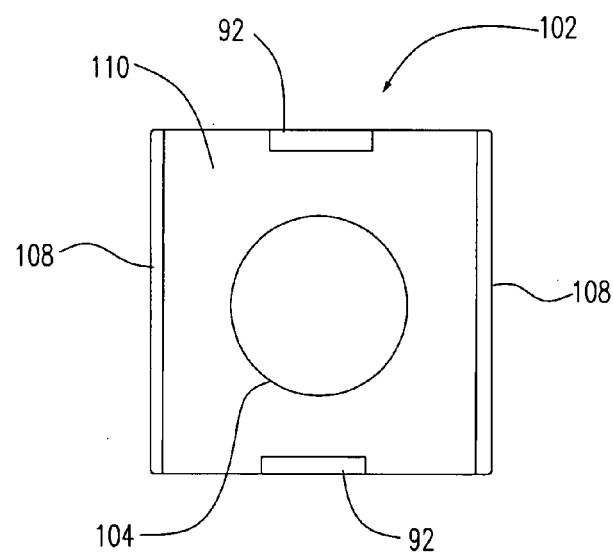
FIG. 12 is a bottom plan view of one embodiment of a base of the locking arrangement depicted in FIG. 10.

Referring now to FIGS. 11, a hole 104 is formed in the base 102 of the locking arrangement 80. In use, the base 102 is positioned at a conduit 126 of the tank 82. As previously described, the conduit 126 is sized to receive the septum cartridge 40 (see FIG. 3). In the illustrated embodiment, the conduit 126 includes a shoulder 106 upon which the base 104 sets. An externally threaded region (shown for example in FIG. 3) of the conduit 126 extends through the hole 104 of the base 102. The threaded nut 30 of the sampling arrangement 10 is threaded onto the externally threaded region for purposes of both securing the septum cartridge 40 within the conduit 126 and capturing the base 102 between the nut 30 and the shoulder 106 of the conduit 126.

Figure 10:
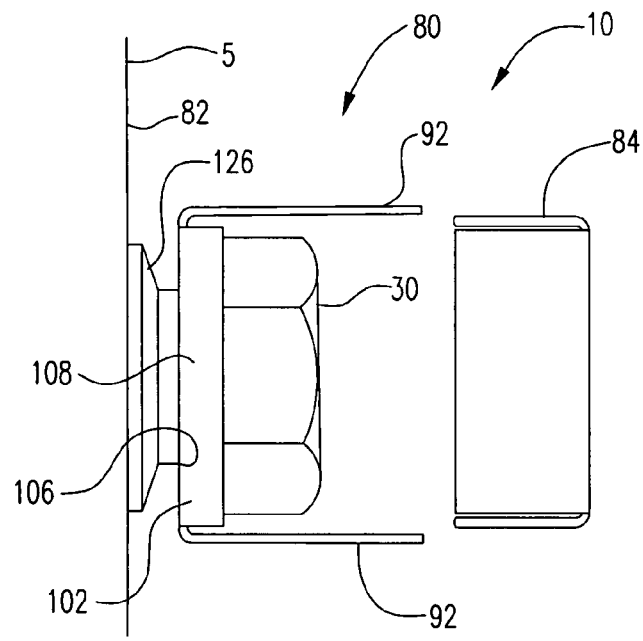
FIG. 10 is a first, partially exploded, side view of one embodiment of a locking arrangement that can be used with the sampling arrangement in accordance with the principles disclosed.

The cover 84 of the locking arrangement 80 is then positioned over the threaded nut 30. As shown in FIGS. 10 and 11, the cover 84 is sized to fit between opposing sides 108 and opposing brackets 92 of the base 102. The opposing sides 108 and the opposing brackets 92 of the base 102 extend outward from a main portion 110 (FIG. 12) of the base 102. In the illustrated embodiment, the sides 108 are shorter than the brackets 92. In use, the sides 108 aid to position the cover 84 in relation to the base 102 so that the cover 84 is retained between the opposing sides 108 of the base 102. The opposing brackets 92 are configured to extend outward from the main portion 110 of the base 102 beyond the cover 84 when positioned assembled as shown in FIG. 13. Each of the brackets 92 includes a hole 94 (FIG. 11) that receives a rod 98 (FIG. 13) of the locking device 86.

Referring to FIG. 13, when the rod 98 of the locking device 86 is positioned through the holes 94 of the brackets 92, the rod 98 extends across the top of the cover 84 so that the cover 84 cannot be removed. Because the cover 84 cannot be removed, the top 41 of the septum cartridge 40 cannot be accessed; similarly, the threaded nut 30 cannot be accessed. In addition, the main portion 110 of the base 102 also prevents access to the threaded nut 30. As can be understood a lock 100, such as a combination lock or key lock, is coupled to the rod 98 to secure the locking device 86 and prevent unwanted access to the septum cartridge 40, the threaded nut 30, and the fluid contained within the tank 82. To access the septum cartridge, the locking device 86 is unlocked, and the cover 84 is simply removed.

Although the locking arrangement 80 has been described with respect to a tank application, it is contemplated that the locking arrangement 80 can further be used in pipe system applications, such as the application shown in FIG. 2, or other fluid transport systems and processing enclosures.

The alternative embodiments herein described may be used in combination with each other or used independent of one another.

The Method of Continuous Sampling, Generally.

In operation, the elbow 12 is installed at a convenient sampling location along a fluid line 20. The elbow is preferably oriented such that the port 22 is in direct fluid contact with the material transferred within the fluid line, to reduce the potential of air drawn during sampling.

The boot 49 of the septum cartridge 40 is placed into the sampling port 22 until the second surface 47 of the cap 45 rests against the outer edge of the sampling port 22. The securing nut 30 is installed onto the conduit of the port 22 to sealingly, operatively secure the septum within the port.

For aseptic sampling, the sampling arrangement, including the port, nut, septum cartridge, etc, are sanitized with a common alcohol prep or other sanitizer. In particular, aseptic sampling is optimized when the cover film 60 is cleansed with a disinfectant, and a sterilized needle 50 is inserted through the disinfected cover film, through an unused guide hole, and through the septum boot.

The needle is preferably directed or slanted toward the center of the septum boot at insertion. This provides greater assurance that the needle penetrates through the entirety of the boot. In effect, the boot essentially squeegees or cleanses the needle of any contaminants missed during initial aseptic disinfectant processes. Directing the needle toward the center of the boot also reduces the possibility of contacting the wall of the extended portion of the elbow.

The needle may be oriented such that the beveled end 51 faces toward the flow of the fluid material to aid in fluid sampling. A pressure differential is applied between the collection container and the fluid line to effect the fluid sampling or material transfer. The pressure differential may be applied in a number of ways. One way is by introducing pressure into the fluid line. Another is by reducing pressure in the connecting conduit or collection container. Any means of generating an adequate pressure differential between the fluid line and the collection container is effective to cause the flow of material through the needle. Other methods of applying the pressure differential and thus effecting the transfer of a sample will be obvious to those skilled in the art.

Material from a tank, for example, thus flows from the fluid line 20, through the needle 50, and into the collection container 18 by way of the connecting conduit 16. In one alternative application, the collection container may be placed into a cooling container 70 of ice or ice water, for example, to reduce or eliminate bacterial growth during the sampling process.

The flow from the fluid line 20 to the collection container 18 may be adjusted to a particular flow or sampling rate by means of the clamp restriction. The flow may likewise be metered wherein the peristaltic pump is assembled to the connecting conduit to regulate the flow.

When the desired sample has been collected, the collection container is removed from the connecting conduit 16 and sealed. The needle 50 is removed from the septum cartridge 40. As the needle end is withdrawn, the material of the boot 49 withdraws into the position held prior to needle penetration. The boot 49 of the septum 40 thus closes and seals the passageway of the now removed needle.

After performing a number of sampling procedures, so that all guide holes have been used, the septum cartridge 40 is removed and discarded. The punctured cover film 60 provides a ready indictor of those guide holes that have been used. A new septum cartridge easily replaces the used septum cartridge for future samplings.

Some Selected Alternate Methods of Use

Once a sample has been collected, the collection container 18 of the present invention may be used to determine any number of product quality defects. One use for determining product quality defects applies to the dairy industry; in particular, to detecting quality defects in dairy fluid products, such as milk, for example.

One such defect is post-pasteurization contamination (PPC). There are many sources of post-pasteurization contamination including inadequate cleaning and sanitizing, contaminated water, engineering defects such as cracked tanks or other equipment components, condensation in compressed air lines, and other sources. Undoubtedly contamination from these sources can result in poor keeping quality, consumer complaints, and reduced profits.

One of the primary causes of dairy product quality defects is post-pasteurization contamination (PPC) with gram-negative psychrotrohic bacteria found in pasteurized milk. In recent years, research has shown that the level of post-pasteurization contamination of gram-negative bacteria in pasteurized milk can be extremely low, but still affect dairy product quality. This research showed that contamination rates as low as one bacterium per liter can cause spoilage and other product defects in a short time if the growth rate of that bacterium is extremely fast. Other research has shown that the growth rate is dependent on storage temperature and oxygen concentrations of the milk. For example, it is possible for gram-negative bacteria to cause quality defects at 7° C. (45 ° F.) in a little as ten days under ideal growth conditions of saturated oxygen in milk.

The disclosed sampling arrangement 10 can be used to effectively monitor dairy processes for the potential of contamination of the gram-negative psychrotrophic bacteria. In particular, to monitor for possible gram-negative bacteria contamination, the arrangement 10 is used to obtain an aseptic fluid sample within the collection container 18 at the discharge of the HTST (High Temperature Short Time) pasteurizing processor. Because of the aseptic design of the sampling arrangement 10, contamination of both the fluid sample and the primary fluid flow during sampling is prevented to preclude the sampling arrangement as a source of bacterial contamination. Typically, the size of the fluid sample is between about 50-500 ml in volume, however, the collection container 18 can aseptically accommodate larger samples of up to about 5 liters.

In one embodiment, the collection container 18 preferably has an oxygen permeability that simulates the level of oxygen to which the fluid product is exposed. For instance, the oxygen permeability preferably simulates the oxygen saturation associated with pre-packing operations and the product packaging within which the fluid will be stored. By this, the collection container 18 allows gram-negative bacteria to grow in the same fashion as the bacteria would in product storage containers. In particular, the oxygen permeability of the collection container 18 promotes the same growth rate of contaminate as there would be in a product that has been fully oxygen saturated through pumping, agitating and filling procedures. The arrangement 10 thereby simulates the storage conditions for purposes of monitoring for gram-negative bacteria without the addition of air or oxygen to a collected sample.

Once the desired fluid sample size is collected, the sample is permitted to incubate for a time period sufficient to allow for low-level contaminants to reach a level that can be counted by conventional laboratory procedures. Typically, the incubation period corresponds to the shelf life of the fluid product. In one method, for example, the fluid sample is incubated for a number of days at 45° F. During the incubation period, oxygen permeates the collection bag to oxygenate the fluid product. A Standard Plate Count is conducted during the incubation period to determine the level of gram-negative bacteria present within the sample. The Standard Plate Count can be repeated any number of times during the incubation period. Methods other than the Standard Plate count for detecting psychrotrophic bacteria (spoilage bacteria) can be used.

To illustrate the oxygen permeability of the collection bag 18, a study of gram-negative psychrotrohic bacteria was conducted at the University of Minnesota's Biological Technology Institute. In this study, a fluid sample of sterilized milk was inoculated with pseudomonas bacteria at a population of about 60 organisms per liter. The inoculated milk was filled in three collection bags and three 60 cc syringes, and then incubated in the refrigerator at 7° C. (45° F.). The three syringes containing inoculated milk served as non-permeable container controls. Bags and syringes containing un-inoculated milk also served as controls (see Table 1 below). In the inoculated collection bags, the presence of the bacteria was clearly evident with six days. In contrast, the inoculated syringes required 21 days to positively confirm the presence of bacteria. By using the disclosed sampling arrangement 10, the time needed to obtain contamination results is significantly shortened due to the oxygen permeability feature of the collection bag 18. Reducing the time needed to detect contamination saves in production costs and reduces product waste associated with continued production of a contaminated product.

TABLE 1

| | Daily cell counts of bacteria (cfu/ml) | | | | | | | | | |
|---|---|---|---|---|---|---|---|---|---|---|
| | Day 0 | 3 | 6 | 7 | 8 | 9 | 10 | 13 | 15 | 21 |
| Control bag 1 | <1 | <1 | <1 | <1 | <1 | <1 | <1 | <1 | | <1 |
| Control bag 2 | <1 | <1 | <1 | <1 | <1 | <1 | <1 | <1 | | <1 |
| Bag 1 | <1 | 1 | 15 | 80 | 169 | 334 | 750 | $2.2 \times 10^6$ | | $6.5 10^7$ |
| Bag 2 | <1 | 1 | 15 | 70 | 110 | 200 | 350 | $1.0 \times 10^6$ | | $10.5 \times 10^7$ |
| Bag 3 | <1 | 2.5 | 13 | 70 | 29 | 100 | 600 | $1.7 \times 10^6$ | | $6.0 \times 10^7$ |
| Control Syr 1 | <1 | <1 | <1 | <1 | <1 | <1 | <1 | <1 | <1 | <1 |
| Control Syr 2 | <1 | <1 | <1 | <1 | <1 | <1 | <1 | <1 | <1 | <1 |

TABLE 1-continued

Daily cell counts of bacteria (cfu/ml)

| | Day 0 | 3 | 6 | 7 | 8 | 9 | 10 | 13 | 15 | 21 |
|---|---|---|---|---|---|---|---|---|---|---|
| Syr 1 | <1 | <1 | <1 | <1 | <1 | 3 | 4 | 3 | <1 | 21.5 |
| Syr 2 | <1 | <1 | <1 | <1 | <1 | 2 | <1 | <1 | <1 | 3.5 |
| Syr 3 | <1 | 1 | <1 | 1 | <1 | 5 | 2 | 1 | <1 | 193 |

Another defect affecting the quality of dairy fluid products is spore-forming bacteria found in pre-pasteurized or raw milk. Raw milk quality can greatly influence the keeping quality of market milk. One of the primary causes of spore-forming bacteria is gram-positive psychrotrohic bacteria. Spore-forming bacteria is generally caused by contamination introduced in pre-pasteurization milk processes. Determining the level of spore-forming bacteria in a fluid product sample provides valuable information for evaluating the associated production, cleaning processes and shelf life.

Research has also shown that the level of spore-forming contamination of gram-positive bacteria in raw milk can be low, but still affect dairy product quality. For instance, spore-forming bacteria has been found to survive heat treatments of up to 176° F. at 10 minute intervals. In fact, the heat treatment in some cases has even activated spore germination and outgrowth in milk. The disclosed sampling arrangement 10 can be used to effectively monitor dairy processes for the potential of contamination of the gram-positive psychrotrophic bacteria.

In particular, to monitor for possible gram-positive bacteria contamination, the arrangement 10 is used to obtain an aseptic fluid sample within the collection container 18. Because of the aseptic design of the sampling arrangement 10, contamination of both the fluid sample and the primary fluid flow during sampling is prevented to preclude the sampling arrangement as a source of spore-forming bacteria contamination.

Spore-forming bacteria is inherent in raw milk, however, an excessive amount of spore-forming bacteria, or the presence of spore-forming bacteria that has an accelerated growth rate is undesirable and will most likely result in unacceptable milk quality at refrigeration temperature. The collection container 18 of the present sampling arrangement 10 has an oxygen permeability that provides a level of oxygen saturation that accelerates the growth rate of spore-forming bacteria. By this, the collection container 18 allows gram-positive bacteria to grow in an accelerated fashion to determine the amount of gram-positive bacteria present.

Once the desired fluid sample size is collected (e.g., up to 5 liters), the sample is permitted to incubate for a time period sufficient to allow for the spore-forming contaminants to grow. For example, in one method, the fluid sample is incubated for a period of time approximate to the standard product shelf life, e.g., 18-24 days, at 45 ° F. During this period, oxygen permeates the collection bag to oxygenate the fluid product. A conventional laboratory procedure, such as a Standard Plate Count, is then conducted after the period of time to determine the level of gram-positive bacteria present within the sample. A level of gram-positive bacteria greater than 10,000,00 counts/ml, for example, would indicate that the spore-forming bacteria present has the potential for causing product quality defects. This information can then be used to re-evaluate production and cleaning process to reduce the likelihood of future quality problems.

To illustrate the oxygen permeability of the collection bag 18, a study of gram-positive psychrotrohic bacteria was conducted at the University of Minnesota's Biological Technology Institute. In this study, a fluid sample of raw milk was collected in the disclosed bag. The bag was incubated for 18-24 days at a temperature of about 7° C. (45° .F). A standard plate count was then conducted. Using gram-stain procedures, the samples having bacteria counts of greater than 10,000,000/ml were identified (see Table 2 below). Identifying the samples having high bacteria counts reduces product waste associated with continued production of a contaminated product.

TABLE 2

Cell counts of bacteria (cfu/ml)

| Sample | Dairy | Bag | Volume L | Week 1 CFU/ml Gram− | Week 1 CFU/ml Gram+ | Week 2 CFU/ml Gram− | Week 2 CFU/ml Gram+ | Week 3 CFU/ml Gram− | Week 3 CFU/ml Gram+ | Week 4 CFU/ml Gram− | Week 4 CFU/ml Gram+ |
|---|---|---|---|---|---|---|---|---|---|---|---|
| Date: | | | | 3/23/2004 | | 3/30/2004 | | 4/7/2004 | | 4/13/2004 | |
| Day: | | | | 7 | | 14 | | 22 | | 28 | |
| 3/16/2004 | Plant B | A | 1.3 | <10 | <10 | <10 | <10 | <10 | <10 | <10 | <10 |
| Tuesday | | B | 1.5 | <10 | <10 | <10 | <10 | <10 | <10 | <10 | <10 |
| Date: | | | | 3/24/2004 | | 3/31/2004 | | 4/7/2004 | | 4/15/2004 | |
| Day: | | | | 7 | | 14 | | 21 | | 29 | |
| 3/17/2004 | Plant A | A | 1.2 | <10 | <10 | <10 | <10 | <10 | $7.56 \times 10^4$ | <10 | $1.0 \times 10^6$ |
| Wednesday | | B | 1.2 | <10 | <10 | <10 | <10 | <10 | $2.33 \times 10^4$ | <10 | $1.93 \times 10^6$ |
| Date: | | | | 3/31/2004 | | 4/7/2004 | | 4/15/2004 | | 4/21/2004 | |
| Day: | | | | 7 | | 14 | | 22 | | 28 | |
| 3/24/2004 | Plant A | A | 1.2 | <10 | <10 | <10 | $3.0 \times 10^2$ | <10 | $1.41 \times 10^6$ | <10 | $1.05 \times 10^7$ |
| Wednesday | | B | 1.2 | <10 | <10 | <10 | $0.4 \times 10^2$ | <10 | $0.95 \times 10^6$ | <10 | $3.1 \times 10^7$ |
| Date: | | | | 4/7/2004 | | 4/14/2004 | | 4/21/2004 | | 4/28/2004 | |
| Day: | | | | 7 | | 14 | | 21 | | 28 | |

TABLE 2-continued

| | | | | Cell counts of bacteria (cfu/ml) | | | | | | | |
|---|---|---|---|---|---|---|---|---|---|---|---|
| | | | Volume | Week 1 CFU/ml | | Week 2 CFU/ml | | Week 3 CFU/ml | | Week 4 CFU/ml | |
| Sample | Dairy | Bag | L | Gram– | Gram+ | Gram– | Gram+ | Gram– | Gram+ | Gram– | Gram+ |
| 3/31/2004 Wednesday | Plant A | A | 1.2 | <10 | <10 | <10 | <10 | <10 | <10 | <10 | <10 |
| | | B | 1.2 | <10 | <10 | <10 | <10 | <10 | <10 | <10 | <10 |
| Date: | | | | 4/9/2004 | | 4/16/2004 | | 4/23/2004 | | 4/30/2004 | |
| Day: | | | | 7 | | 14 | | 21 | | 28 | |
| 4/2/2004 Friday | Plant B | A | 1.0 | <10 | <10 | <10 | $7.7 \times 10^2$ | <10 | $6.7 \times 10^5$ | <10 | $2.5 \times 10^6$ |
| | | B | 1.1 | <10 | <10 | <10 | $5.8 \times 10^2$ | <10 | $4.96 \times 10^5$ | <10 | $6.5 \times 10^6$ |
| Date: | | | | 4/22/2004 | | 4/29/2004 | | 5/6/2004 | | 5/12/2004 | |
| Day: | | | | 7 | | 14 | | 21 | | 27 | |
| 4/15/2004 Thursday | Plant B | A | 1.1 | <10 | <10 | <10 | <10 | <10 | <10 | <10 | $6 \times 10$ |
| | | B | 1.2 | <10 | <10 | <10 | <10 | <10 | <10 | <10 | <10 |

The above specification, examples and data provide a complete description of the manufacture and use of the invention. Many embodiments of the invention can be made according to the disclosed principles.

I claim:

1. A fluid system, comprising:
   a) a transportable fluid vessel having an aperture that provides access to an interior volume;
   b) an aseptic sampling arrangement configured to provide aseptic sampling of a fluid contained within the interior volume of the transportable fluid vessel, the aseptic sampling arrangement including a septum and a securing element, the septum being secured within the aperture of the fluid vessel by the securing element, the septum including a penetrable body constructed for penetration of a needle therethrough; and
   c) a locking arrangement that provides selective access to the aseptic sampling arrangement.

2. The fluid system of claim 1, wherein the transportable fluid vessel is a tanker truck.

3. The fluid system of claim 1, wherein the locking arrangement includes:
   a) a base;
   b) a cover sized to fit over the septum; and
   c) a security device that secures the cover in relation to the base.

4. The fluid system of claim 3, wherein the base of the locking arrangement prevents access to the securing element of the aseptic sampling arrangement.

5. The fluid system of claim 4, wherein the base is positioned over the aperture of the fluid vessel prior to securing the septum within the aperture via the securing element.

6. The fluid system of claim 5, wherein the base of the locking arrangement has a hole sized to receive a conduit that defines the aperture of the fluid vessel.

7. The fluid system of claim 4, wherein the septum and the securing element are enclosed within the base and the cover to prevent unwanted access to the internal volume of the transportable fluid vessel.

8. The fluid system of claim 7, wherein the base includes sides extending outward from a main portion, and wherein the cover is sized to fit between the sides of the base to enclose the septum and the securing element.

9. The fluid system of claim 3, wherein the base includes opposing extensions projecting outward from a main portion, and wherein the cover is sized to fit between the extensions.

10. The fluid system of claim 9, wherein the opposing extensions project outward from the main portion a distance beyond the cover when the cover is secured in relation to the base.

11. The fluid system of claim 10, wherein the opposing extensions define openings through which the security device extends to secure the cover in relation to the base.

12. The fluid system of claim 11, wherein the security device includes a rod that extends through the openings of the extensions of the base to prevent removal of the cover.

13. The fluid system of claim 12, wherein the security device includes a lock coupled to the rod to secure the security device relative to the base.

14. The fluid system of claim 1, wherein the septum comprises:
   a) a penetrable body;
   b) a cap piece; and
   c) a penetrable layer at least partially covering a portion of the cap piece.

15. The fluid system of claim 1, wherein the securing element is a threaded nut.

16. A method of providing selective aseptic access to a transportable fluid enclosure, the method comprising the steps of:
   a) positioning a septum of an aseptic sampling arrangement within an aperture of the transportable fluid enclosure;
   b) securing the septum within the aperture of the fluid enclosure with a securing element;
   c) enclosing the septum and the securing element within a locking arrangement to prevent unwanted access to the septum and the securing element;
   d) securing the locking arrangement to permit only selective access to the septum and the securing element of the aseptic sampling arrangement.

17. The method of claim 16, wherein the step of positioning the septum within an aperture of the transportable fluid enclosure includes positioning the septum within the aperture of a tanker truck.

18. The method of claim 16, wherein the step of securing the locking arrangement includes securing a cover of the locking arrangement relative to a base of the locking arrangement.

19. The method of claim 18, further including positioning the base over the aperture of the transportable fluid enclosure prior to securing the septum within the aperture of the fluid enclosure.

20. The method of claim 18, wherein the step of enclosing the septum and the securing element includes enclosing the septum and the securing element within the base and the cover of the locking arrangement.

21. The method of claim 20, further including positioning the cover between sides of the base to enclose the septum and the securing element.

22. The method of claim 18, wherein the step of securing the locking arrangement includes positioning a security device through openings defined by opposing extensions that project outwardly from the base of the locking arrangement.

23. The method of claim 22, wherein the step of positioning the security device includes positioning a rod through the openings defined by the extensions of the base.

24. The method of claim 23, further including locking a lock coupled to the rod of the security device to prevent removal of the cover.

\* \* \* \* \*